(12) United States Patent
Biicchi et al.

(10) Patent No.: US 10,912,661 B2
(45) Date of Patent: Feb. 9, 2021

(54) ARTIFICIAL HAND

(71) Applicants: UNIVERSITA' DI PISA, Pisa (IT); FONDAZIONE ISTITUTO ITALIANO DI TECNOLOGIA, Genoa (IT)

(72) Inventors: Antonio Biicchi, Massa (IT); Manuel Giuseppe Catalano, Pisa (IT); Giorgio Grioli, Pisa (IT); Manolo Garabini, Ceprana (IT); Cristina Piazza, Trapani (IT); Cosimo Della Santina, Pontedera (IT)

(73) Assignees: UNIVERSITA' DI PISA, Pisa (IT); FONDAZIONE ISTITUTO ITALIANO DI TECNOLOGIA, Genoa (IT)

( * ) Notice: Subject to any disclaimer, the term of this patent is extended or adjusted under 35 U.S.C. 154(b) by 137 days.

(21) Appl. No.: 16/302,227

(22) PCT Filed: May 9, 2017

(86) PCT No.: PCT/IB2017/052684
§ 371 (c)(1),
(2) Date: Nov. 16, 2018

(87) PCT Pub. No.: WO2017/199127
PCT Pub. Date: Nov. 23, 2017

(65) Prior Publication Data
US 2019/0269528 A1 Sep. 5, 2019

(30) Foreign Application Priority Data

May 16, 2016 (IT) .......................... UA2016A003457

(51) Int. Cl.
*A61F 2/58* (2006.01)
*A61F 2/68* (2006.01)
(Continued)

(52) U.S. Cl.
CPC ................ *A61F 2/586* (2013.01); *A61F 2/68* (2013.01); *B25J 15/0009* (2013.01); *B25J 15/10* (2013.01);
(Continued)

(58) Field of Classification Search
CPC .... A61F 2/586; A61F 2/68; A61F 2/72; A61F 2/583; A61F 2/585; A61F 2002/747; A61F 2002/587; B25J 15/0009; B25J 15/10
(Continued)

(56) References Cited

U.S. PATENT DOCUMENTS

2005/0102037 A1\* 5/2005 Matsuda .............. B25J 19/0075
623/24
2015/0351936 A1\* 12/2015 Mosadegh ........... B25J 15/0023
623/26
2016/0121489 A1\* 5/2016 Moore ................. B25J 15/0009
294/198

FOREIGN PATENT DOCUMENTS

EP 0 045 818 A1 2/1982
EP 1 195 151 A1 4/2002
(Continued)

*Primary Examiner* — Suba Ganesan
*Assistant Examiner* — Aren Patel
(74) *Attorney, Agent, or Firm* — Vorys, Sater, Seymour & Pease

(57) ABSTRACT

An artificial hand is provided. The artificial includes phalanges suitable to reproduce at least one finger, hinges hinging a first element identifying a phalanx to a second element identifying a second phalanx, and an implementation mechanism suitable to command a reciprocal rotation between the hinges defining a mutual rotation speed between the first and second element. The hinges define different damping coefficients so that, during a mutual rotation of the first and second element, they are subject to distinct damping forces opposing mutual rotation and proportional to the
(Continued)

mutual rotation speed so as to vary the movement of the artificial hand as a function of the mutual rotation speed.

15 Claims, 5 Drawing Sheets

(51) Int. Cl.
    *B25J 15/10*     (2006.01)
    *B25J 15/00*     (2006.01)
    *A61F 2/72*     (2006.01)
    *A61F 2/50*     (2006.01)
    *A61F 2/74*     (2006.01)

(52) U.S. Cl.
    CPC ......... *A61F 2/72* (2013.01); *A61F 2002/5006* (2013.01); *A61F 2002/5038* (2013.01); *A61F 2002/747* (2013.01)

(58) Field of Classification Search
    USPC .............................................. 623/26, 57–65
    See application file for complete search history.

(56) References Cited

FOREIGN PATENT DOCUMENTS

WO     2007/076763 A2     7/2007
WO     2014/111843 A2     7/2014

\* cited by examiner

*Fig. 1a*
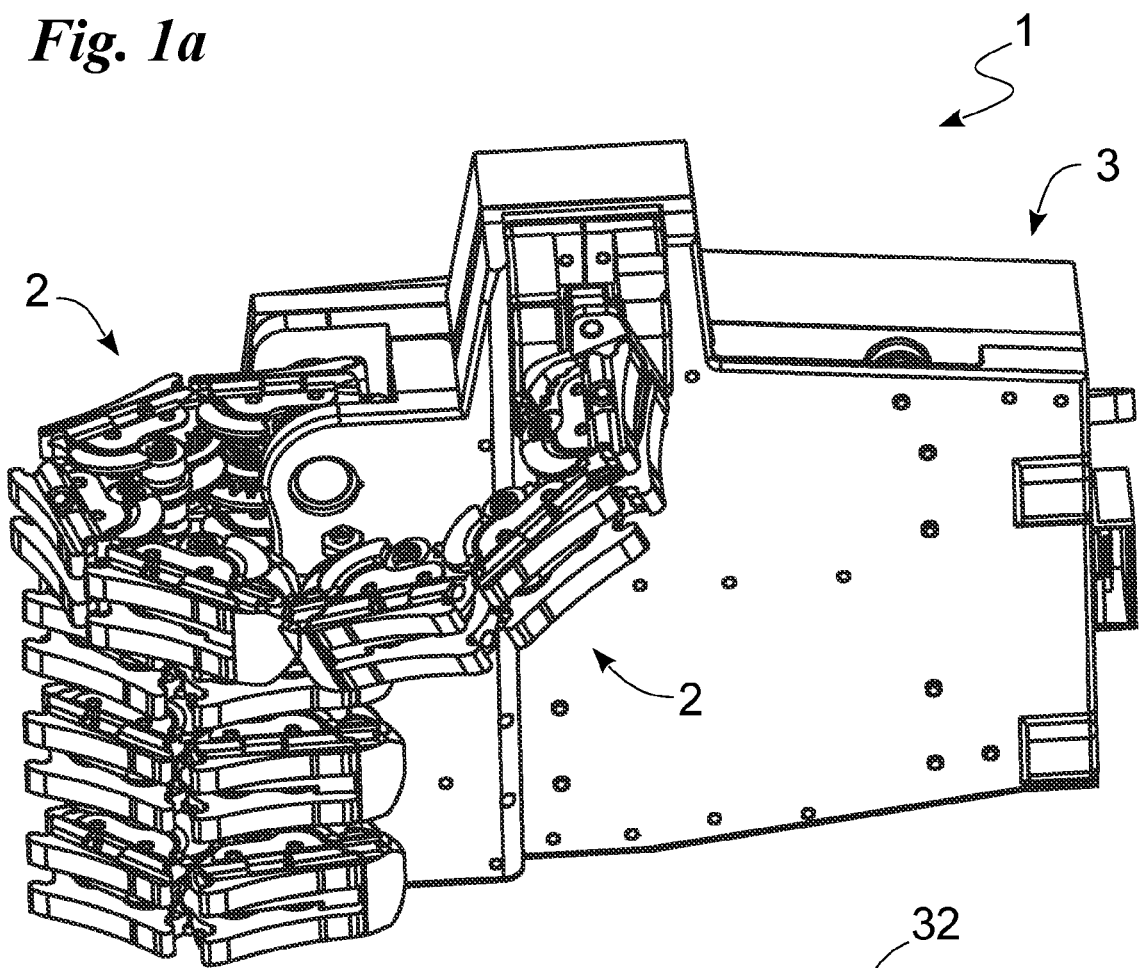
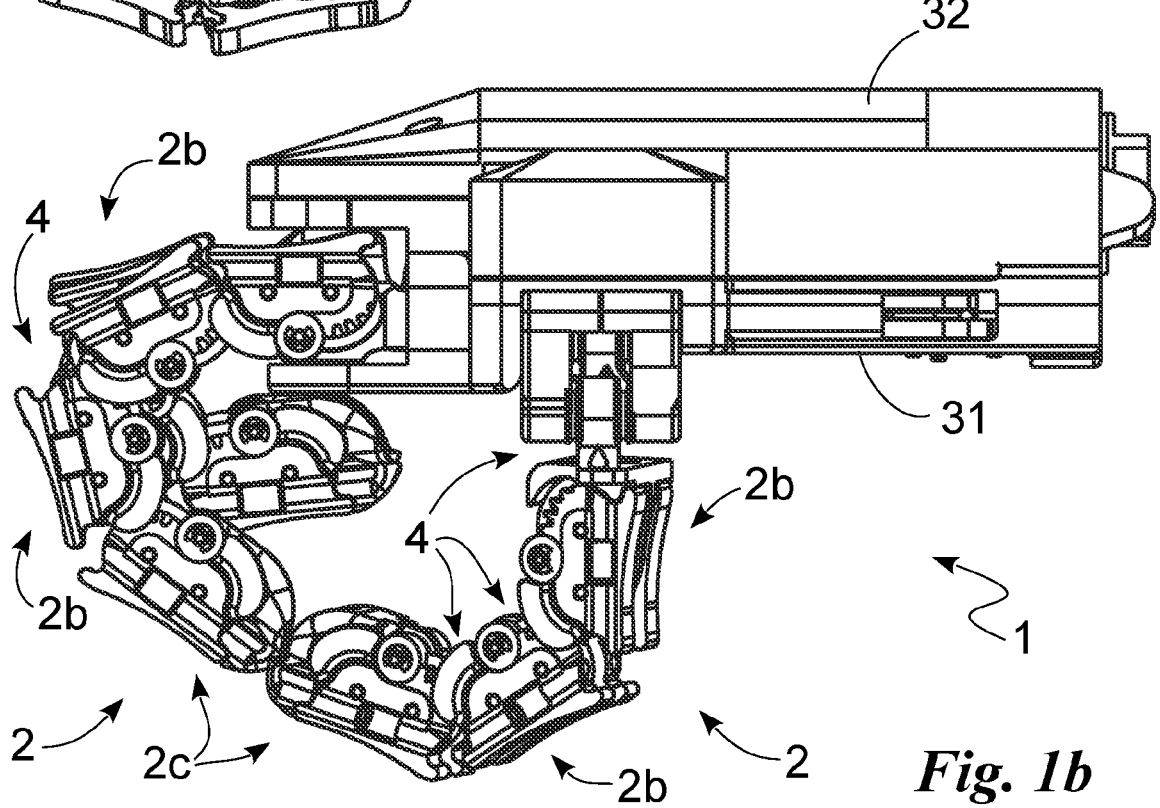
*Fig. 1b*

ARTIFICIAL HAND

The present invention relates to an artificial hand of the type specified in the preamble to the first claim.

In particular, the present invention relates to a sub-actuated robotic hand with possible prosthetic application, i.e. a myoelectric hand having a smaller number of actuators than degrees of freedom and able to reproduce the movements of a human hand.

As is known, artificial hands, and specifically prosthetic hands fall into two main classes, passive and active.

Passive hands aim to reconstruct a mutilated body segment in order to restore bodily integrity with specific focus on appearance. These hands are characterized by a rigid structure with non-motorised phalanges. They are not able to grip.

Active hands have mechanical and/or electronic components which by articulating together the parts forming the hand, are able to reproduce various poses and thus different grips.

Active artificial hands are in turn divided into two groups.

The first group is characterized by a number of actuators equal to the number of degrees of freedom and a control unit which independently controls each actuator so that the hand is able to assume any position/grip.

Given the almost infinite number of positions which can be assumed these artificial hands require an input that, having to define each degree of freedom, is extremely rich in information and particularly complicated to manage.

It should be emphasised how this problem is evident in the case of prosthetic hands where the command of the hand can be imparted with residual contractions of the muscles of the arm, and thus the number of commands is extremely limited.

In addition, on account of the large number of actuators, these artificial hands have large dimensions and are complex both to construct and to programme.

As a result in sub-actuated artificial hands the number of actuators is smaller than the number of degrees of freedom.

An example of a sub-actuated artificial hand provides an actuator for each finger associated with the individual phalanges so as to control the rotation thereof. The fingers can thus be moved independently of each other.

In some cases, the sub-actuated artificial hand may provide for a single actuator which, associated to the various phalanges, allows them to command a simultaneous flexing.

The prior art mentioned above has several significant drawbacks.

An important drawback of sub-actuated artificial hands is that they define only a limited number of poses.

In particular, these sub-actuated artificial hands are not able to change the speed of mutual rotation between the phalanges/fingers connected to a single actuator.

This aspect is obvious in the case of sub-actuated prosthetic hands where the variability of data commands in input is extremely reduced.

It may be emphasised how, as a result, the aforesaid drawback is also evident in all artificial hands with a smaller number of actuators than degrees of freedom. In fact, despite increasing the number of actuators, sub-actuated artificial hands will always have degrees of freedom which, being connected to a single actuator, will have an invariable speed ratio.

Another important drawback is therefore the limited number of poses and, consequently, of grips that can be obtained with a sub-actuated artificial hand.

For example the invariability of the speed ratio between the degrees of freedom makes it nearly impossible to change the order in which the fingers close forming a first or assuming a pose or grip.

Another drawback is that the above mentioned drawbacks make it hard for a sub-actuated prosthetic hand of the prior art to satisfy the expectations of the patient.

In this situation the technical purpose of the present invention is to devise an artificial hand able to substantially overcome the drawbacks mentioned.

Within the sphere of said technical purpose one important aim of the invention is to have an artificial hand able to define an increasing number of poses.

In particular, an important purpose of the invention is to make an artificial hand that allows the user to vary the relative speeds of the degrees of freedom and thereby change the pose/grip of the hand.

An additional purpose of the invention is to develop an artificial hand that can better meet the expectations of the patient.

The technical purpose and specified aims are achieved by an artificial hand as claimed in the appended claim 1.

Preferred embodiments are evident from the dependent claims.

The characteristics and advantages of the invention are clearly evident from the following detailed description of a preferred embodiment thereof, with reference to the accompanying drawings, in which:

FIG. 1a shows one pose of the artificial hand according to the invention;

FIG. 1b is a second view of the pose in FIG. 1a;

FIG. 2b is a second view of the pose in FIG. 2a;

FIG. 4b shows a cross-section of the assembly in FIG. 4a;

Figure 2A:
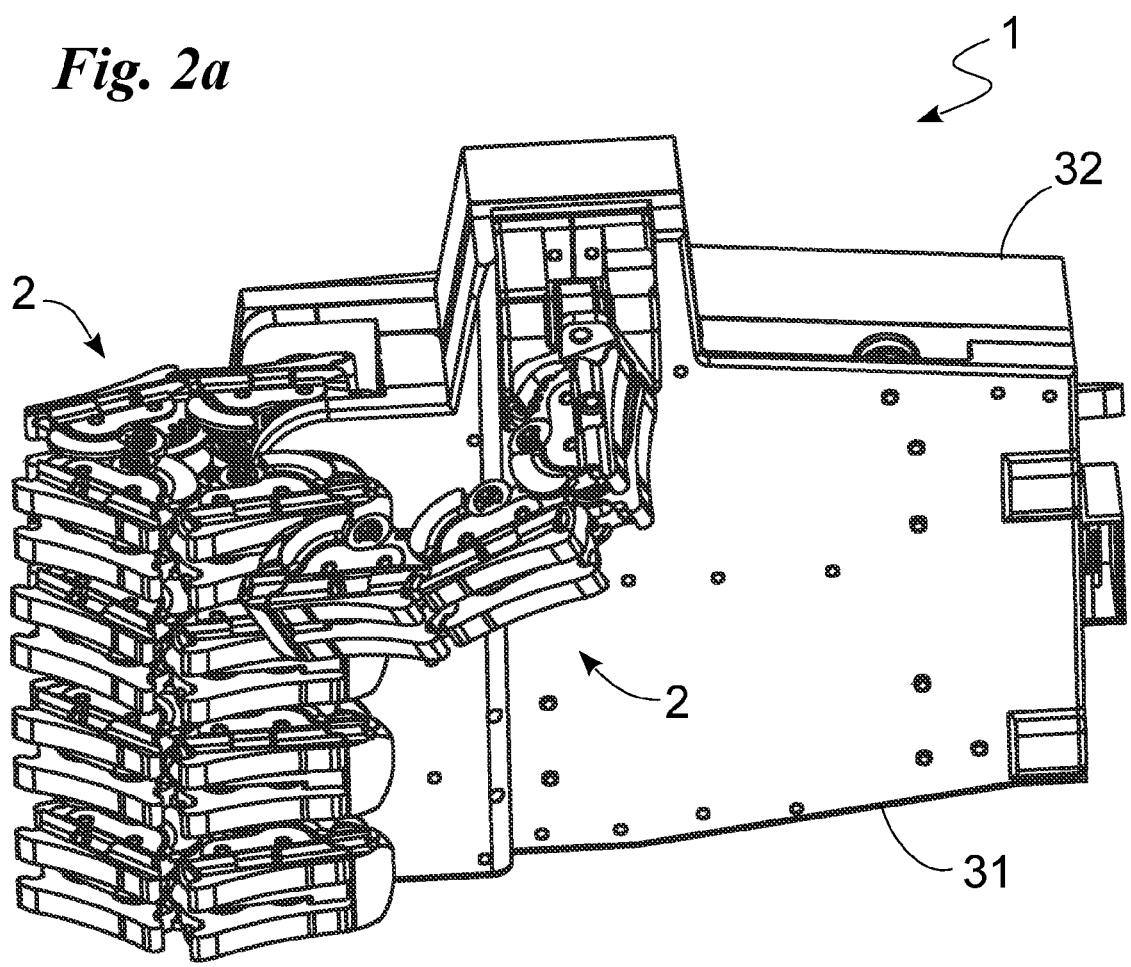
FIG. 2a shows a second pose of the artificial hand.
Figure 2B:
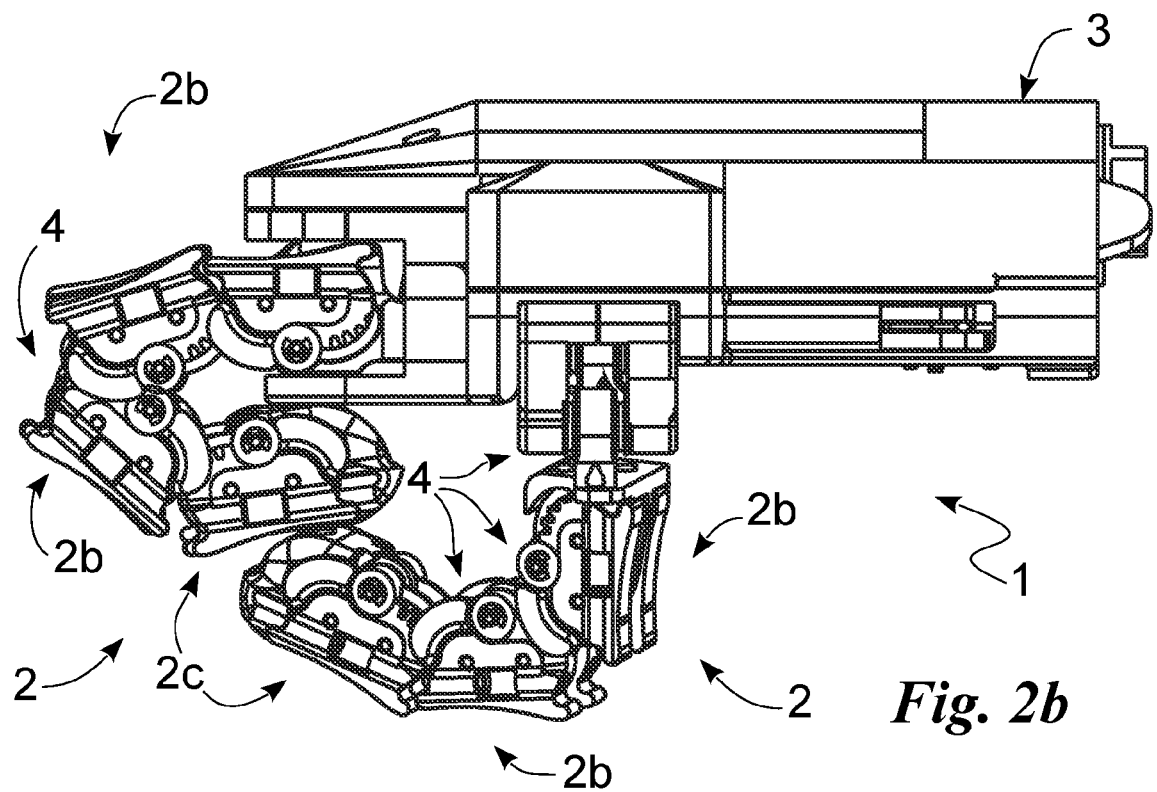

With reference to the Figures mentioned, reference numeral 1 globally denotes the artificial hand according to the invention.

It may be a robotic hand or preferably a hand suitable to be controlled by the contraction of a muscle, i.e. a prosthetic or myoelectric hand. In particular, the artificial hand 1 may identify a partial hand prosthesis (e.g. consisting of one or more fingers) or a total hand prosthesis.

Figure 3:
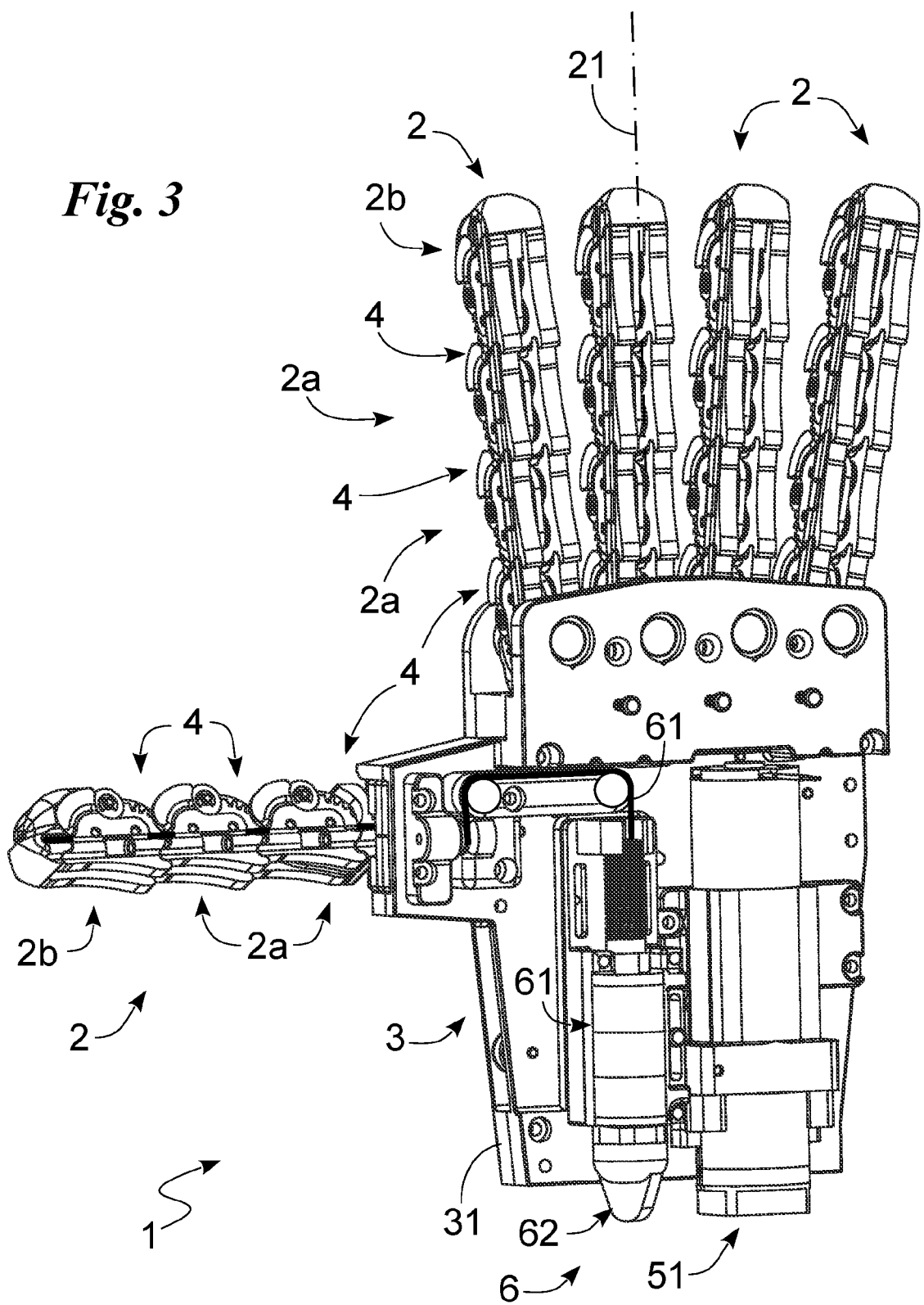
FIG. 3 shows another view of the artificial hand according to the invention.

The artificial hand 1 may comprise a plurality of phalanges able to reproduce fingers of each hand defining its own longitudinal axis 21 defined with the finger stretched out as in FIG. 3.

In particular, the artificial hand 1 may comprise one or more fingers 2 and for each finger 2, one or more phalanges.

Each finger 2 may comprise at least one bottom phalanx 2a; and a tip phalanx 2b defining the fingertip. In particular, a finger 2 comprises two bottom phalanges 2a, appropriately placed one after the other along the longitudinal axis of the finger, and a tip phalanx 2b.

The artificial hand 1 may comprise a palm 3 to which one or more phalanges 2a and 2b and, specifically, a bottom phalanx 2a for each finger 2 are joined.

The palm comprises a base body 31 to which one or more components of the hand 1 and a casing 32 suitable to be coupled to the base body 31 defining a housing volume can be engaged.

The artificial hand 1 comprises one or more hinges 4 each hinging a first element of the artificial hand 1 to a second element of the artificial hand 1 allowing their mutual rotation; and at least one implementation mechanism 5 suitable to command a reciprocal rotation between the hinges 4 defining a reciprocal rotation speed between the first and second element.

It is to be emphasised that each hinge 4 identifies a degree of freedom of the sub-actuated artificial hand 1.

The first element of the artificial hand 1 is identifiable in a phalanx 2a and/or 2b.

The second element of the artificial hand 1 is identifiable in a phalanx 2a and/or 2b. Preferably it is identifiable in a phalanx 2a and/or 2b or in the palm 3.

A hinge 4 may be placed between a bottom phalanx 2a and the palm 3; between a bottom phalanx 2a and a tip phalanx 2b; and/or between two bottom phalanges 2a. More precisely, the artificial hand 1 comprises five hinges 4 placed between bottom phalanges 2a and palm 3, five hinges 4 placed between the bottom phalanges 2a of each finger 2; and five hinges 4 placed between the bottom phalanges 2a and adjoining tip phalanx 2b of each finger 2.

Each hinge 4 is suitable to define a mutual axis of rotation between the first and second element preferably almost perpendicular to the longitudinal axis.

Each hinge 4 may comprise two arched surfaces 41, appropriately toothed, one integral with the first element and one with the second element and suitable to engage and slide reciprocally allowing a mutual rotation between the first and second element; and appropriately elastic means 42 suitable to clamp said elements to each other ensuring contact between the arched surfaces 41.

The elastic means 42 are suitable to exert a force of attraction between the first and second element.

Figure 4A:
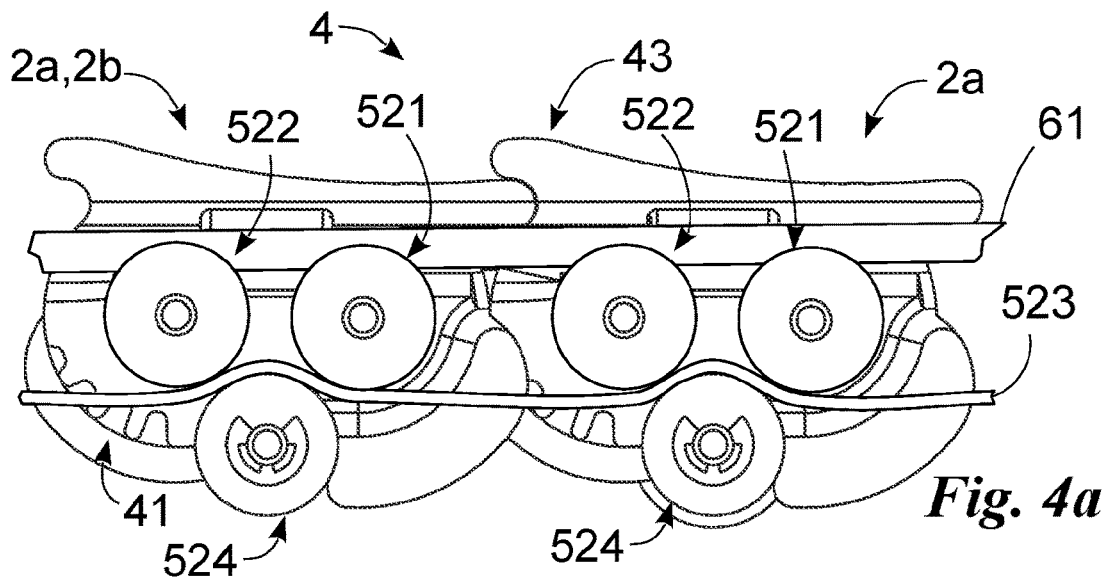
FIG. 4a shows an assembly of the artificial hand.
Figure 4B:
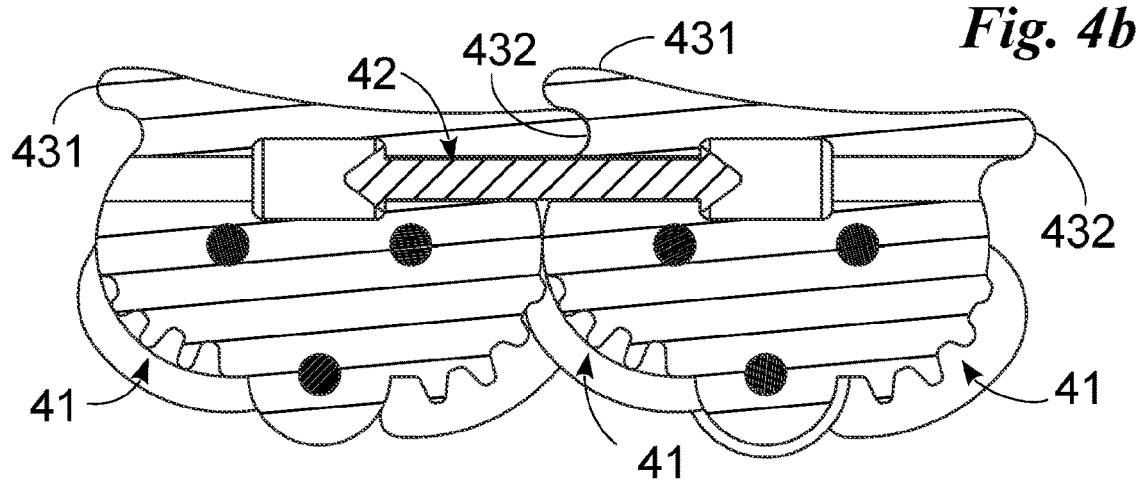

It should be noted that the elastic means 42 as described in more detail below, work in opposition to a closing of the hand, i.e. to an angular juxtaposition between the first and second element and, thus the realization of a gripping pose, thus favouring a spreading out between first and second element. The elastic means 42 connect two contiguous phalanges 2a and/or 2b and/or a bottom phalanx 2a to the palm 3. The elastic means 42 may comprise at least one closed loop or in some cases, two closed loops. Alternatively, they may comprise at least one elastic segment (FIG. 4b) and in detail two elastic segments.

Each hinge 4 may comprise an end stop 43 suitable to limit the angle of divergence between the first and second element.

The end stop 43 may comprise a first tooth 431 protruding from the first element and a second tooth 432 protruding from the second element and suitable to abut with the first tooth 431 limiting the rotation between first and second element.

In order to control the mutual rotation between first and second element the implementation mechanism 5 comprises an actuation system 51 of the hand 1 and at least one distribution member 52 of the motion from the implementation system 51 to each hinge 4 defining a rotation speed between first and second element.

The implementation system 51 comprises at least one motor suitable to generate a movement that, through the distribution member 52, determines a mutual rotation between first and second element.

In particular, the artificial hand 1 is sub-actuated and therefore the implementation system 51 has a smaller number of motors than the number of degrees of freedom, and thus of hinges 4.

In particular, it may comprise a single motor or alternatively two motors preferably independent of each other.

Said at least one motor can be connected to the palm 3 and in particular, to the base 31 and is available in the housing volume.

It is identifiable in a motor, preferably electric and more preferably a servomotor, i.e. a motor fitted with a control circuit by means of which to control the motor itself.

In some cases, the artificial hand 1 may be sub-actuated and of the body-powered type and, therefore, the implementation system 51 is suitable to define the motion of the hand 1 taken from a portion of the body. As a result, the implementation system 51 may provide for a chest harness and, for example, include at least one tendon suitable to be attached to a portion of the body, for example, to convey the motion of the shoulder 52 to the distribution member and thus to the hinges 4.

The distribution member 52 comprises a plurality of pairs of pulleys each pair placed at each hinge 4.

In detail each pair of pulleys includes at least a first pulley 521 connected to the first element, and at least a second pulley 522 connected to said second element.

Preferably, each pair of pulleys comprises a first pulley 521 and a second pulley 522. Alternatively, it comprises two first pulleys 521 and two second pulleys 522 facing a first pulley 521.

The distribution member 52 further comprises at least one cable 523 sliding in all the pulleys 521 and 522 and suitable to be controlled by the implementation system 51.

The pulleys 521 and 522 of a pair are mutually facing so that between them there are no parts in contact with the cable 523. As a result the portion of cable 523 subtended between the pulleys 521 and 522 has substantially the same tension.

They may be the same friction or, alternatively, the pulleys 521 and 522 of at least one hinge 4 may be different friction.

The expression different friction means that the pulleys 521 and/or 522 may have different friction coefficients, suitably rotational, with the cable 523 and/or with the element they are engaged with. Advantageously the pulleys 521 and/or 522 have different friction coefficients from the element they are engaged to so that at least some of the pulleys 521, 522 transmit, to the element they are joined to, a different torque, appropriately that transmitted by one or more of the other pulleys 521 and/or 522 to the corresponding element, resulting in different mutual rotation speeds between the elements.

It is to be noted how, advantageously, having pulleys 521 and/or 522 with different friction allows a tension drop on the cable 523 and as a result the tension on the cable 523 is less in the last contact (or detachment) point on the pulley with respect to that of the cable 523 at the point of first contact of the cable 523 on said pulley.

As a result, the pulleys 521 and/or 522 with different friction are subjected by the cable 523 to different torques from each other and hence transmit to the corresponding element a different torque.

The pulleys 521 and 522 can be made of a material chosen from steel, PVC, polymer materials, aluminium and ceramic.

The pulleys 521 and 522 associated with the same hinge 4 define substantially parallel axes and, in detail, substantially coincident with each other. In particular, the pulleys 521 and 522 of a finger have substantially parallel axes to each other and substantially perpendicular to the longitudinal axis of the finger itself.

To ensure contact between cable 523 and pulleys 521 and 522 the distribution member 52 may comprise at least one idler wheel 524 suitable to incline the cable 523 with respect to the line joining the points of last contact of the cable 523 on the pulleys 521 and 522.

In particular, the implementation mechanism 5 comprises a plurality of idler wheels 524 each interposed between each pair of adjacent pulleys 521 and 522.

The idler wheel 56 is identifiable in a pin, a sheave.

The at least one cable 523 is designed to slide individually inside all the pulleys 521 and 52, i.e. suitable to come into contact only one with each pulley 521 and 522 in the sub-actuated artificial hand 1.

It is made of a material with an elastic coefficient equal to at least 50 Gpa and, specifically, to 100 Gpa. It is made of a material chosen from steel, PVC and a synthetic fibre such as, preferably, Dyneema (Gel Spun Polyethylene).

The distribution member 52 may comprise a single cable 523 sliding through all the pulleys 521 and 522.

Said single cable 523 cable is open and has the ends engaged to the implementation system 51.

For example, the single cable 53 has the ends connected to two motors which can thus exert on it either two torques/forces equal to each other and, therefore, two tensions at the two ends of the cable 523 equal to each other; or two distinct torques/forces and thus two different tensions at both ends of the cable 523.

Alternatively, the cable 523 may have the ends integral with a single actuator which can apply to the cable 523 equal or distinct tensions.

In a further alternative, the single cable may be controlled by the at least one tendon of the implementation system 51.

The artificial hand 1 may comprise a control unit suitable to control the operation of the hand and in particular the at least one implementation system.

In particular, the artificial hand 1 may be a prosthetic or myoelectric hand. It may comprise at least one biometric sensor suitable to detect a signal/command coming from the patient and therefore the control unit is suitable to control the hand 1 as a function of said signal/command detected by the biometric sensor.

This signal may be an electromyographic signal (variation of electrical potential during a contraction of a muscle) and, therefore, the biometric sensor may be an EMG sensor (also known as a myoelectric sensor) suitable to measure a variation of potential in a muscle and transmit to the control unit a signal proportional to such measurement.

Preferably, the EMG sensor is suitable to determine, based on the intensity of the variation of potential, the contraction speed of the muscle and, thus command the at least one implementation system 51 to impose a reciprocal rotation speed on the hinges 4 proportional to the contraction speed of the muscle.

Consequently, in the case of a slow contraction of the muscle, the EMG sensor commands a low reciprocal rotation speed of the hinges 4. Conversely, in the case of high speed muscle contraction, the EMG sensor commands a high reciprocal rotation speed of the hinges 4.

The EMG sensor is in itself known.

Alternatively or in addition, the biometric sensor may be selected from: inertial sensors where the command is generated by the movement of a part of the body (e.g. shoulder of the healthy arm); EEG sensor measuring a variation of cortical electrical potential and, thus, extracting the signal directly at brain level; epineural electrodes suitable to send the control unit an electrical signal taken from the peripheral nervous system (e.g. connecting to the nerves of an amputated arm). Advantageously, the artificial hand 1 may comprise at least one damper 6 associated with one or more hinges 4 so as to define the damping coefficient of the hinge 4. The hinges 4, by means of said dampers 6, define different damping coefficients determining, during a reciprocal rotation between the first and the second element, distinct damping forces (to be precise torques) opposing such reciprocal rotation and proportional to the reciprocal rotation speed of the elements.

These damping forces/torques thus vary the reciprocal rotation speed between the first and the second element and thus the movement of the artificial hand 1 as a function of such reciprocal rotation speed.

This concept can be demonstrated by the balance of the torques acting in an artificial hand 1 expressed in the following equation:

$$T^T CT\dot{q} + Eq = R^T u + w$$

where
- T represents the matrix of the transmission ratios between the angles of the hinges 4 and the deformations of the dampers 6;
- $\dot{q}$ is the vector of the reciprocal rotation speed between the first and second element;
- C is a diagonal matrix of the damping coefficients of the hinges 4;
- E is a diagonal matrix of the elastic coefficients (i.e. of the elastic means 42);
- q is the vector of the angles between the first and second element;
- R Is the matrix of transmission ratios from the implementation mechanism 5 to the hinges 4 (this matrix represents how the drive torque given by the implementation mechanism 5 is discharged on each hinge 4)
- u is the vector of the force of the implementation mechanism 5;
- w is the vector of the torques at the hinges 4 due to external forces acting on the artificial hand 1 and to be precise on the phalanges 2a and 2b and, if present, on the palm 3.

From the equation it can be seen how the contribution of the elastic means 42 is directly proportional to the elongation of said elastic means 42 and hence the angle between the first element and the second element, the contribution of the dampers 6 (expressed by $T^T CT\dot{q}$) is directly proportional to the reciprocal rotation speed between the elements.

Therefore, any low reciprocal rotation speeds result in an irrelevant contribution of the dampers 6 and thus negligible forces/damping torques between the first element and the second element.

In contrast, by increasing the reciprocal rotation speed, the contribution of the dampers 6 is increased making the damping forces/torques between the first and second elements significant. Thus, having hinges 4 with different damping coefficients, damping forces/torques of different entities are created, resulting in a different reciprocal rotation between the elements and hence a different movement of the sub-actuated artificial hand 1.

Figure 6A:
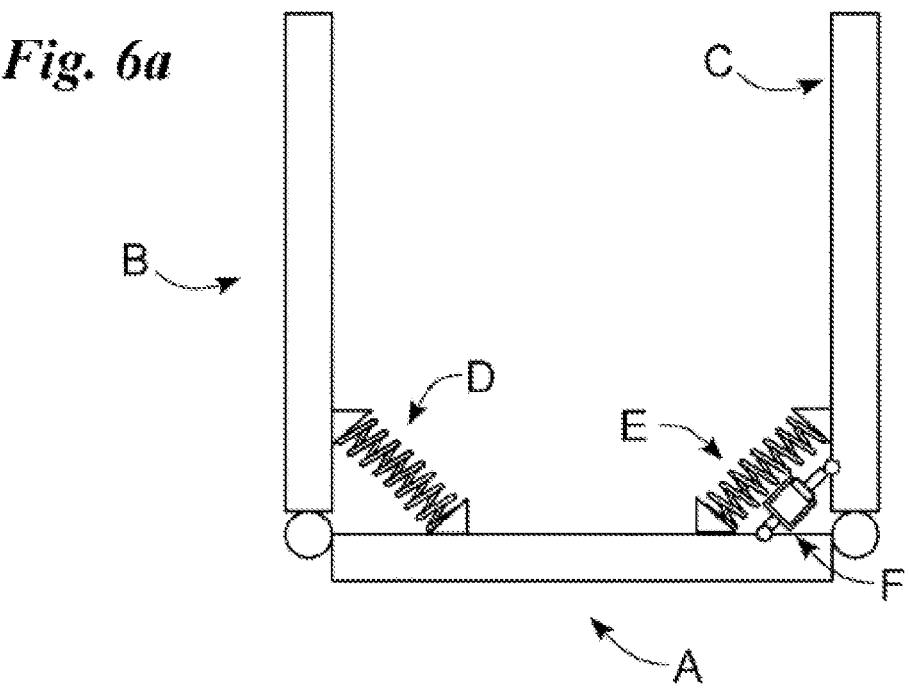
FIG. 6a shows a schematic diagram of the hand according to the invention.

To further clarify this concept the example in FIG. 6a represents a support A, identifiable for example in the palm 3 or in a phalanx 2a or 2b; a first rod B hinged to the support A and identifiable in a phalanx 2a and/or 2b; a second rod C hinged to the support A and identifiable in a phalanx 2a and/or 2b. In detail, the second rod C is hinged to the support A defining a different damping coefficient to that between the first rod B and support A. Therefore, between the first rod B and support A, only a first spring D is interposed, while a second spring E is placed between the second rod C and the support A, the same as the first spring D, and a damper F.

Figure 6B:
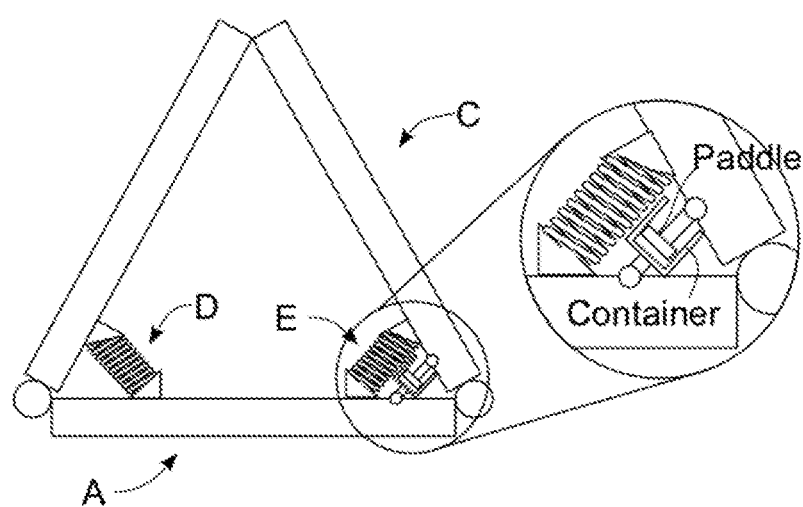
FIG. 6b is the schematic diagram of FIG. 6a in a different moment.

By simultaneously turning the rods B and C with respect to the support A at low speeds, the second rod C is subject to a damping torque rod generated by the damper F of negligible magnitude. As a result, the rods B and C are subjected to the same forces so they have the same speed and position themselves as in FIG. 6b.

Figure 6C:
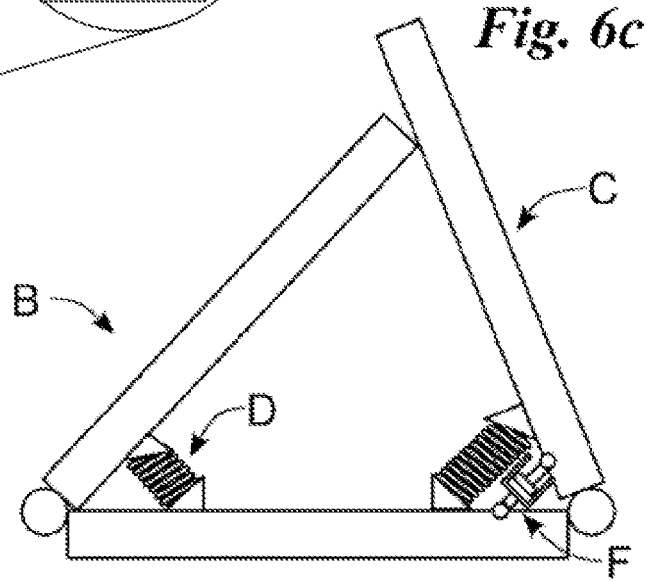
FIG. 6c is the schematic diagram of FIG. 6a in a further moment.

By simultaneously turning the rods B and C with respect to the support A at high speeds, the second rod C is subject to a damping torque of elevated magnitude. As a result, the second rod C is slowed by the damping torque of the damper F with respect to the first rod B which thus rests on the support A shown in FIG. 6c.

In a first embodiment, the damping coefficients of the hinges 4 of a finger 2 may be equal to each other and different from those of the hinges 4 of the other fingers 2. For example, one or more dampers 6 associated with the hinges 4 of a finger such as the thumb may have the same damping coefficient but different from the hinges 4 of one or more of the other four fingers.

In a second embodiment, the hinges 4 of a finger 2 may have distinct damping coefficients and therefore be associated with distinct dampers 6. For example, the hinges 4 between the bottom phalanges 2a and palm 3 may all have a first damping coefficient; the hinges 4 between the bottom phalanges 2a may have a second damping coefficient distinct from the first, the hinges 4 between the bottom 2a and tip phalanges 2b may have a third damping coefficient distinct from the first and second coefficient.

In a third embodiment, the combination of the first and second embodiments described above, the damping coefficients may vary both between the hinges 4 of a finger 2 and between the hinges 4 of different fingers.

The variation of the damping coefficient between the hinges 4 can be obtained by providing hinges 4 associated with a damper 6 and hinges 4 not associated with a damper 6. Alternatively or in addition, the variation of the damping coefficient may be obtained by varying the damper 6 from hinge 4 to hinge 4.

It should also be noted that, as described below, one or more dampers 6 can define a fixed damping coefficient (i.e. non-modifiable) or variable (i.e. modifiable and therefore adjustable).

By way of example some dampers 6 utilisable in the sub-actuated artificial hand 1 are shown below.

A first example of dampers 6 may comprise at least one duct 61 (FIG. 4a) extending between the first and second elements of at least one hinge 4 and integral with said elements; and at least one fluid at least partially filling said duct 61.

In detail, as shown in FIG. 3, the hinges 6 of at least one finger (e.g., the thumb) may provide a single damper 6 and, precisely, a single duct 61 passing through said at least one finger and integral with the elements of said hinges 4 and hence the phalanges 2a and 2b and, preferably, the palm 3.

The duct 61 is identifiable in a tube, suitably flexible, integral with the phalanges 2a and/or 2b, and optionally identifiable in a recess in said phalanges.

In this first example, the damper 6 comprises at least one tank 62 of said fluid and at least one pump 63 suitable to move said fluid between said tank 62 and said duct 61.

The tank 62 and the pump 63 may be integral with the palm 3 and, precisely, the base body 31 and available in the housing volume.

In the case of fluid identifying a liquid, the pump 63 is suitable to fill or empty the duct 61 varying the damping coefficient; while if the fluid is a gas the pump 63 is suitable to vary the damping coefficient depending on the pressure inside the duct 61.

It should also be noted that it is possible to have a damper 6 comprising various fluids, several ducts; and, for each duct 61 a tank 62 of one of said fluids and a pump 63.

Said various fluids may be liquids of different viscosity. Alternatively, the various fluids may be different gases.

In other examples, the damper 6 may be suitable to act on a single hinge 4 and comprise a kinematic mechanism connected to the first and second elements of a hinge 4 so as to be actuated during a reciprocal rotation of said elements; and a fluid in which said kinematic mechanism is at least partially immersed so that, during a reciprocal rotation of said elements, said kinematic mechanism moves in said fluid, generating, by viscous friction, a damping force/torque.

As a result, in a second example, a damper 6 may comprise a cylinder hinged to the first element and defining an appropriately tight containment volume of a fluid; and a piston hinged to the second element and suitable to slide, during said reciprocal rotation, into said cylinder and thus into the fluid generating a damping force/torque.

Figure 5:
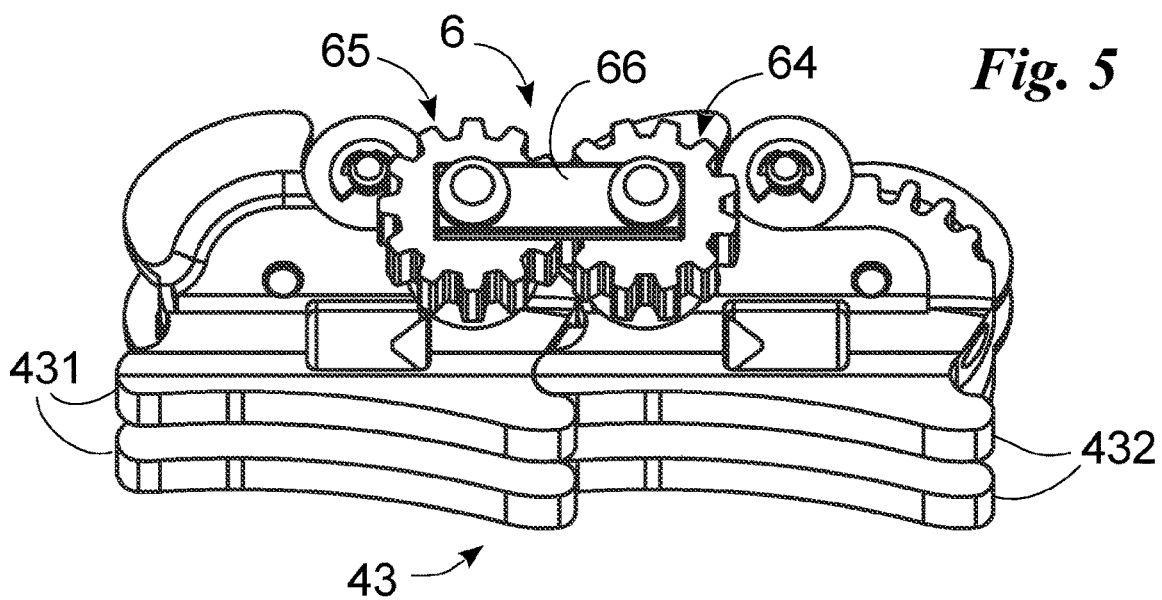
FIG. 5 is an alternative assembly to that of FIGS. 4a and 4b.

In a third example, a damper 6 (FIG. 5) may comprise a first toothed wheel 64 integral with the first element; a second toothed wheel 65 integral with the second element and meshing with the first toothed wheel 64 so that the wheels 64, 65 are able to rotate during the mutual rotation of said elements; a fluid appropriately liquid; a container of said fluid integrally connected to the first element; and at least a paddle immersed in said fluid and integral with the first wheel 64 so that, during the rotation of the first wheel 64, the paddle can rotate in the fluid generating a damping force/torque.

Preferably, the damper 6 may further comprise an additional fluid suitably liquid; an additional container of said additional fluid integrally connected to the second element; and at least an additional paddle immersed in said additional fluid and integral with the second wheel 65 so that during the rotation of the second wheel 65 the additional paddle can rotate in the additional fluid and also generate a damping force/torque.

The damper 6 may comprise only one type of liquid or two different liquids.

Lastly, the damper 6 of said third example may comprise a constraint 66 between the first toothed wheel 64 and the second toothed wheel 65 suitable to prevent a reciprocal rotation between said wheels 64 and 65 avoiding a disengagement of said wheels 64 and 65.

In a fourth example, the damper 6 and the elastic means 42 can be made in one piece and, therefore, the variation of the damping coefficient can be obtained by varying the construction material of the hinges and/or the cross-section of the elastic means 6.

In a fifth example, the damper 6 and the cable 52 may coincide and therefore the variation of the damping coefficient can be obtained using a cable with portions made in different materials and/or having a different cross-section.

It is to be noted how an artificial hand 1 may comprise dampers 6 made according to two or more of the above examples.

The functioning of a sub-actuated artificial hand, described above in a structural sense, is as follows.

The functioning is described with reference to an artificial hand 1 where the hinges 4 of the thumb have the same damping coefficients, while the hinges 4 of the other four fingers have damping coefficients equal to each other but lower than those of the thumb.

Initially, the artificial hand 1 is presented with the fingers extended (FIG. 3), i.e. with the hinges 4 defining an angle between first and second element substantially equal to 180°.

In the first case, the operator controls, for example by a muscular contraction detected by the EMG sensor, a slow closing of the hand 1, i.e. with slow speeds at the hinges 4. In this case, the dampers 6 generate damping forces/torques of negligible intensity and do not affect the speed of rotation of the phalanges 2a, 2b defining a first closed pose for the artificial hand 1.

In a second case, the operator controls, for example by a distinct muscle contraction, a rapid closing of the sub-actuated artificial hand 1. The EMG sensor detects a greater variation of potential and commands the implementation mechanism 5 to impose a reciprocal rotation speed between first and second element greater than that of the previous case.

On account of the greater speed between the elements and hence the hinges 4, the dampers 6 generate damping forces/torques of non-negligible intensity which can influence the reciprocal rotation speed between the first and the second element.

In particular, the advantageously different damping coefficients give rise to damping forces/torques of a different modulus from hinge 4 to hinge 4. These different damping forces/torques influence differently from each other the rotation speed of the hinges 4 leading to a second closed pose of the artificial hand 1 in which the fingers and, specifically, the phalanges 2a and 2b have a different arrangement than the first closed pose.

The invention achieves important advantages.

In fact, a first important advantage is that the artificial hand 1 is able to assume different poses even if sub-actuated.

In fact, the innovative idea of having a hand 1 with different damping coefficients makes it possible to vary in a non-proportional manner the relative rotation speeds and hence to have phalanges 2a and/or 2b which, depending on the speed modulus, are able to assume a speed in proportion advantageously different from that of the other phalanges 2a and/or 2b.

This aspect is of paramount importance in the case of an artificial hand 1 identifiable in a prosthetic or myoelectric hand where, despite a limited variety of command signals, it is possible to command the hand to assume different poses.

It is to be noted how the possibility of varying the damping coefficient, for example by modifying the pressure of the fluid in the duct 61, allows the artificial hand 1 to further increase the number of possible poses.

Another advantage is that the sub-actuated artificial hand 1, although defining a plurality of poses, requires a very simple and intuitive control unit and, furthermore, a simple implementation mechanism 5 with respect to a known hand able to assume such plurality of poses.

A further advantage is therefore the low cost of the hand 1.

A non-secondary advantage is that the sub-actuated artificial hand 1, which can assume multiple grip positions, is easily utilisable for numerous applications/uses in the field for example of industrial automation.

Moreover, this advantage of the artificial hand 1 is that it can constitute a sub-actuated prosthetic hand able to fully satisfy the patient's expectations.

Variations may be made to the invention without departing from the scope of the inventive concept described in the independent claims and in the relative technical equivalents. In said sphere all the details may be replaced with equivalent elements and the materials, shapes and dimensions may be as desired.

The invention claimed is:

1. An artificial hand, comprising:
    phalanges configured to reproduce at least a finger;
    hinges hinging a first element identifying one of said phalanges to a second element identifying one of said phalanges distinct from said first element;
    an implementation mechanism configured to command a reciprocal rotation between said hinges defining a mutual rotation speed between said first element and said second element,
    wherein said hinges define different damping coefficients so that, during a mutual rotation between said first element and said second element, said hinges are subject to distinct damping forces opposing said mutual rotation and proportional to said mutual rotation speed so as to vary the movement of said artificial hand as a function of said mutual rotation speed.

2. The artificial hand according to claim 1, further comprising a plurality of said at least one finger, wherein said damping coefficients of said hinges of one of said at least one finger are equal to each other and different from said damping coefficients of said hinges of the other of said fingers.

3. The artificial hand according to claim 1, wherein said damping coefficients of said hinges of one of said at least one finger are different from each other.

4. The artificial hand according to claim 1, further comprising at least one damper associated with at least one of said hinges and configured to define said damping coefficient of said at least one hinge.

5. The artificial hand according to claim 4, wherein said damper comprises at least one duct integral with said first element and said second element of said at least one hinge and at least a fluid configured to at least partially fill said duct.

6. The artificial hand according to claim 5, wherein said damper comprises at least one tank of said fluid and at least one pump configured to move said fluid between said tank and said duct.

7. The artificial hand according to claim 6, wherein said fluid is a gas and wherein said pump is configured to vary said damping coefficient as a function of the pressure inside said duct.

8. The artificial hand according to claim 4, wherein said damper comprises a first toothed wheel integral with said first element; a second toothed wheel integral with said second element, and meshing with said first toothed wheel so that said wheels rotate during the mutual rotation of said elements; a fluid; a container of fluid integral with said first element; and at least a paddle immersed in said fluid and integral with said first wheel so that, during said mutual rotation between said first element and said second element, said paddle rotates in said fluid generating said damping forces.

9. The artificial hand according to the claim 8, wherein said damper comprises a constraint between said first toothed wheel and said second toothed wheel configured to prevent a mutual rotation of said wheels.

10. An artificial hand, comprising:

phalanges configured to reproduce at least a finger;

hinges hinging a first element identifying one of said phalanges to a second element identifying one of said phalanges distinct from said first element;

an implementation mechanism configured to command a reciprocal rotation between said hinges defining a mutual rotation speed between said first element and said second element, wherein said hinges define different damping coefficients so that, during a mutual rotation between said first element and said second element, said hinges are subject to distinct damping forces opposing said mutual rotation and proportional to said mutual rotation speed so as to vary the movement of said artificial hand as a function of said mutual rotation speed; and said artificial hand comprises at least one damper associated with at least one of said hinges and configured to define said damping coefficient of said at least one hinge; and wherein said damper comprises a first toothed wheel integral with said first element; a second toothed wheel integral with said second element, and meshing with said first toothed wheel so that said wheels rotate during the mutual rotation of said elements; a fluid; a container of fluid integral with said first element; and at least a paddle immersed in said fluid and integral with said first wheel so that, during said mutual rotation between said first element and said second element, said paddle rotates in said fluid generating said damping forces.

11. The artificial hand according to claim 10, further comprising a plurality of said at least one finger, wherein said damping coefficients of said hinges of one of said at least one finger are equal to each other and different from said damping coefficients of said hinges of the other of said fingers.

12. The artificial hand according to claim 10, wherein said damping coefficients of said hinges of one of said at least one finger are different from each other.

13. The artificial hand according to claim 10, wherein said damper comprises at least one tank of said fluid and at least one pump configured to move said fluid between said tank and said duct.

14. The artificial hand according to claim 13, wherein said fluid is a gas and wherein said pump is configured to vary said damping coefficient as a function of the pressure inside said duct.

15. The artificial hand according to claim 10, wherein said damper comprises a constraint between said first toothed wheel and said second toothed wheel configured to prevent a mutual rotation of said wheels.

* * * * *

UNITED STATES PATENT AND TRADEMARK OFFICE
CERTIFICATE OF CORRECTION

PATENT NO. : 10,912,661 B2
APPLICATION NO. : 16/302227
DATED : February 9, 2021
INVENTOR(S) : Antonio Biicchi et al.

Page 1 of 1

It is certified that error appears in the above-identified patent and that said Letters Patent is hereby corrected as shown below:

In the Claims

Claim 8, Column 10, Line 53, change as follows:
The artificial hand according to claim 5, wherein said Signed and Sealed this
Eleventh Day of May, 2021

Drew Hirshfeld
*Performing the Functions and Duties of the*
*Under Secretary of Commerce for Intellectual Property and*
*Director of the United States Patent and Trademark Office*